(12) United States Patent
Tang et al.

(10) Patent No.: US 8,617,567 B2
(45) Date of Patent: Dec. 31, 2013

(54) FUNGUS POLYOSE COMPOSITION WITH IMMUNITY ENHANCING EFFECT AND APPLICATION THEREOF

(76) Inventors: Jian Tang, Guangdong (CN); Xiaofei Xu, Guangdong (CN); William Ma, Guangdong (CN); Zhen Luo, Guangdong (CN); Wenjuan Fang, Guangdong (CN)

( * ) Notice: Subject to any disclaimer, the term of this patent is extended or adjusted under 35 U.S.C. 154(b) by 417 days.

(21) Appl. No.: 12/631,868

(22) Filed: Dec. 7, 2009

(65) Prior Publication Data

US 2011/0021770 A1    Jan. 27, 2011

(30) Foreign Application Priority Data

Jul. 23, 2009 (CN) .......................... 2009 1 0041320

(51) Int. Cl.
*A61K 36/06* (2006.01)
*A61K 36/09* (2006.01)
*C07H 1/00* (2006.01)

(52) U.S. Cl.
USPC .................................. 424/195.15; 536/123.1

(58) Field of Classification Search
None
See application file for complete search history.

(56) References Cited

U.S. PATENT DOCUMENTS

2006/0013825 A1* 1/2006 Kristiansen ............... 424/195.15
2008/0199488 A1* 8/2008 Tani ......................... 424/195.15

OTHER PUBLICATIONS

Borchers et al. (1999) Proc. Soc. Ex. Biol. Med. vol. 221; pp. 281-293.*
Zheng et al. (2005) International Immunopharmacology 5; 811-820.*
De Baets et al. (2001) Biotechnology Letters 23: 1361-1366.*
Chihara et al. (1970) Cancer Research 30, pp. 2776-2781.*

* cited by examiner

*Primary Examiner* — Chris R Tate
*Assistant Examiner* — Russell Fiebig
(74) *Attorney, Agent, or Firm* — George G. Wang; Bei & Ocean

(57) ABSTRACT

The present invention relates to a compound fungus polyose with the effect of enhancing immunity. The compound is prepared with raw material as follows: *Lentinus edodes* 8~100, *Poria cocos* 15~100, *Dictyophora indusiata* 10~200, *Tremella fuciformis* 15~80, *Paecilomyces hepiali* mycelium 2~50. The present invention also relates to the use of compound fungus polyose in preparing health dietary supplements for enhancing immunity. The compound fungus polyose of present invention is characterized in that it uses the edible (medicinal) fungus rich in activity polyose as the main raw material and matches various kinds of polyose components, enhances body's immunity in multiple ways, and has beneficial health effects on those who are sub-health. The health dietary supplements prepared with compound fungus polyose of present invention as the main effective component has an evident effect on enhancing immunity and a satisfactory effect on the health of those who are sub-health.

12 Claims, No Drawings

FUNGUS POLYOSE COMPOSITION WITH IMMUNITY ENHANCING EFFECT AND APPLICATION THEREOF

FIELD OF THE INVENTION

The present invention relates to a compound fungus polyose with effects of enhancing immunity, which is prepared from edible (medicinal) fungus as raw material, and the present invention further relates to uses of the compound fungus polyose for its effects of enhancing immunity.

BACKGROUND OF THE INVENTION

Fungus polyose is a type of active polyose, having effects of controlling differentiation of cell division and regulating cell growth and aging. It is isolated from fungus sporophore, mycelium, or fermentation broth, and generally is a macromolecule polymer formed from the linkage of monosaccharides with more than ten molecules by the glucosidic bond. Molecule monomers of fungus polyose, are largely bound with β(1-3) and β(1-6) glucosidic bonds, and form chain molecules with a helical configuration. Scientific experiments have indicated that fungus polyose has strong anti-tumor activities, strong inhibitory effects on cancer cells, and plays important roles in the process of immunoregulation, lowering blood pressure, reducing blood lipid, anti-thrombus, invigorating stomach and hepatoprotection. Now, fungus polyose has been generally applied to the clinical treatment of diseases, for example immune deficiency diseases, autoimmune diseases and tumor, and so on. Therefore, it is known as an important biological response modifier.

DETAILED DESCRIPTION OF THE INVENTION

An object of the present invention is to provide a compound fungus polyose having the effect of enhancing immunity, which is prepared with traditional technology with edible (medicinal) fungus as the main raw material. The compound fungus polyose has an evident effectiveness on enhancing immunity, and has a beneficial health effect to sub-health persons.

Another object of the present invention is to provide a use of the compound fungus polyose, prepared according to the present invention, for preparing health dietary supplements with the purpose of enhancing immunity.

The compound fungus polyose with immunity-enhancing properties supplied by present invention is prepared with *Lentinus edodes, Poria cocos, Dictyophora indusiata, Tremella fuciformis* and *Paecilomyces hepiali* mycelium as raw material.

The weight proportion of the raw material used for preparing the compound fungus polyose of present invention is: *Lentinus edodes* 8~100, *Poria cocos* 15~100, *Dictyophora indusiata* 10~200, *Tremella fuciformis* 15~80, *Paecilomyces hepiali* mycelium 2~50.

A preferable proportion according to weight of the raw material used for preparing the compound fungus polyose of present invention is: *Lentinus edodes* 10~50, *Poria cocos* 45~80, *Dictyophora indusiata* 30~150, *Tremella fuciformis* 25~55, *Paecilomyces hepiali* mycelium 10~50.

A more preferable proportion according to weight of the raw material used for preparing the compound fungus polyose of present invention is: *Lentinus edodes* 30, *Poria cocos* 60, *Dictyophora indusiata* 90, *Tremella fuciformis* 40, *Paecilomyces hepiali* mycelium 20.

Furthermore, present invention provides a use of the compound fungus polyose in preparing health dietary supplements with the effect of enhancing immunity. The health dietary supplements prepared with the compound fungus polyose as the main active component by conventional technology can be processed into various dosage forms, such as capsules, tablets, powders, drug granules, oral liquid, and so on.

*Lentinus edodes* is the sporohore of *Lentinus edodes* (berk.) Sing. According to 《The Dictionary of Chinese Herbal Medicine》, the nature of *Lentinus edodes* is sweet in flavor and neutral in nature, benefiting the stomach's Qi. Lentinan is an important medicinal component. Lentinan, which is a typical activator of T cells, can promote the creation of cytotoxic T lymphocyte (CTL) both in vivo and in vitro, improve the potency of CTL, enhance Delayed Hypersensitivity (DTH) of the mice with normal immune function or the immuno-compromised, and enhance the activity of the antibody dependent cytotoxic cells (ADDC). Lentinan has strong anti-tumor activity and regulates the immune function of the body as widely reported in the literature.

Chinese caterpillar fungus (*Cordyceps sinens* (BerK.) Sacc) is a special valuable medicinal fungus in China. In order to ease the severe problem between supply and demand, using fluid deep submerged fermentation to culture Chinese caterpillar fungus mycelium to substitute the natural Chinese caterpillar fungus has gained general acceptance. *Paecilomyces hepiali* belongs to the Chinese caterpillar fungus strains which can be used in dietary supplements sanctioned by the Ministry of Public Health of China. In 1972, the Institute of Materia Medica, Chinese Academy of Medical Sciences, started to research artificial culturing of Chinese caterpillar fungus mycelium. They were the first to isolate the CS-4 strains of *Paecilomyces hepiali* from fresh Chinese caterpillar fungus [*Cordyceps sinensis* (Berk)Sacc] produced in Hualong of Qinghai province. Then from the culture of artificial fermentation they obtained the fermented Chinese caterpillar fungus mycelium. Research has proved that the *Paecilomyces hepiali* mycelium obtained by fermentation contains 19 kinds of amino acids, such as nucleosides (Adenosine, Adenosine), cordycepic acid (D-mannitol), ergosterol, Chinese caterpillar fungus polyose, and minosuccinic acid, etc. The pharmacological empirical study showed that Chinese caterpillar fungus polyose has the effect of enhancing immunity of the subject.

*Poria cocos* is the dried sclerotium of *Porio cocos* (Schw.) Wolf of Polyporaceae fungus. According to pharmacopoeia, *Poria cocos*, which is sweet in flavor and light and mild by nature, can strengthen the spleen, regulate the stomach, and tranquilize the heart. *Poria cocos* contains polyose. The pachyman of *Poria cocos* can enhance the immune function of the normal mice and the tumor-bearing mice, and enhance the phagocytizing function of mice's macrophages. Caplendusing *Poria cocos* polyose can improve cytoimmunity function of elderly people. Many animal experiments proved that, just as with other fungus polyose, *Poria cocos* polyose has a very evident anti-tumor effect. Now, it is well known that it is accomplished by strengthening the body's immune function, and activating the immune surveillance system.

*Dictyophora indusiata* is the sporophore of *Dictyophora indusiata* of Phallaceae fungus. According to the book 《Chinese Herbal》, *Dictyophora indusiata* is sweet and slightly bitter in taste, cool in nature, and has the effects of reinforcing Qi and nourishing Yin. Its pharmacological actions indicate that the extract of *Dictyophora indusiata* has an anti-cancer effect. The plylose isolated from *Dictyophora indusiata* has an inhibitory action to sarcoma S180 of mice. Du Yiguang discovered, from the research on the effect of mycelium extracting solution of deep submerged fermentation of *Dictyophora indusiata* on anti-tumor and enhancing mice's immune function, that the mycelium extracting solution of deep submerged fermentation of *Dictyophora indusiata* can evidently enhance the phagocytize ability of macrophages, increase the weight of mice's thymus gland and spleen, and enhance mice's immunities.

*Tremella fuciformis* is the sporophore of *Tremellaceae Tremella* fuciformis. 《Chinese Herbal》 records that, *Tremella fuciformis* which is sweet in flavor and tasteless and neutral in nature, has the effect of invigorating engendering fluids, moisturizing the lungs and nourishing the stomach. *Tremella fuciformis* contains *Tremella fuciformis* polyose, *Tremella fuciformis* spore polyose, glucoprotein, acidity heteroglycan, etc. For the past few years, there were many researches carried out in and outside of China on its main component, *Tremella fuciformis* polyose, and the research shows that *Tremella fuciformis* polyose has many pharmacologic actions. *Tremella fuciformis* polyose can increase the weight of normal mice's immune organs, enhance the mice's humoral immunity function and cellular immunity function, promote the secretion of cytokine, and has an anti-tumor effect. With a dosage of 0.75 g/kg, the compound fungus polyose prepared with *Tremella fuciformis* polyose and *Lentinus edodes* polyose, can obviously enhance the humoral immunity and cellular immunity function of mice bearing cancer, and obviously promotes non-specific immunity. Lin Xiaoming, etc. fed mice with the extracting solution of water of *Tremella fuciformis* and *Poria cocos*, and found that it could promote the proliferating of mice's T-Lymphocytes and the secreting of IL-2.

The compound fungus polyose of present invention is characterized in that it uses the edible (medicinal) fungus rich in active polyose as the main raw material, rationally combines and matches various types of polyoses components, enhances the body's immunity in multiple ways, and has a satisfactory effect on of the health of sub-health individuals. The dietary supplement prepared with compound fungus polyose of present invention as the main effective component has an significant effect on enhancing immunity and a beneficial effect on the health of those suffering from sub-health.

The present invention is further illustrated by the following specific embodiment and pharmacodynamics study results.
Description of Preferred Embodiments The invention is further illustrated by the following examples. It is to be understood that the examples are provided for illustrative purposes only. They are not to be construed as limiting the scope or content of the invention in any way. It is, of course, intended to cover any nonessential variations and modifications according to present invention as defined by the appended claims.

EXAMPLE 1

The compound fungus polyose with effects of enhancing immunity was prepared with the following raw materials proportioned by weight: *Lentinus edodes* 30 kg, *Poria cocos* 60 kg, *Dictyophora indusiata* 90 kg, *Tremella fuciformis* 40 kg, *Paecilomyces hepiali* mycelium 20 kg.

EXAMPLE 2

The compound fungus polyose with effects of enhancing immunity was prepared with the following raw materials proportioned by weight: *Lentinus edodes* 10 kg, *Poria cocos* 80 kg, *Dictyophora indusiata* 100 kg, *Tremella fuciformis* 60 kg, *Paecilomyces hepiali* mycelium 45 kg.

EXAMPLE 3

The compound fungus polyose with effects of enhancing immunity was prepared with the following raw materials proportioned by weight: *Lentinus edodes* 40 kg, *Poria cocos* 80 kg, *Dictyophora indusiata* 70 kg, *Tremella fuciformis* 50 kg, *Paecilomyces hepiali* mycelium 25 kg.

EXAMPLE 4

The compound fungus polyose with effects of enhancing immunity was prepared with the following raw materials proportioned by weight: *Lentinus edodes* 60 kg, *Poria cocos* 100 kg, *Dictyophora indusiata* 120 kg, *Tremella fuciformis* 20 kg, *Paecilomyces hepiali* mycelium 20 kg.

EXAMPLE 5

The compound fungus polyose with effects of enhancing immunity was prepared with the following raw materials proportioned by weight: *Lentinus edodes* 80 kg, *Poria cocos* 50 kg, *Dictyophora indusiata* 130 kg, *Tremella fuciformis* 30 kg, *Paecilomyces hepiali* mycelium 15 kg.

EXAMPLE 6

The compound fungus polyose with effects of enhancing immunity was prepared with the following raw materials proportioned by weight: *Lentinus edodes* 90 kg, *Poria cocos* 30 kg, *Dictyophora indusiata* 70 kg, *Tremella fuciformis* 30 kg, *Paecilomyces hepiali* mycelium 35 kg.

EXAMPLE 7

The compound fungus polyose with effects of enhancing immunity was prepared with the following raw materials proportioned by weight: *Lentinus edodes* 15 kg, *Poria cocos* 50 kg, *Dictyophora indusiata* 30 kg, *Tremella fuciformis* 30 kg, *Paecilomyces hepiali* mycelium 20 kg.

EXAMPLE 8

The compound fungus polyose with effects of enhancing immunity was prepared with the following raw materials proportioned by weight: *Lentinus edodes* 70 kg, *Poria cocos* 90 kg, *Dictyophora indusiata* 180 kg, *Tremella fuciformis* 70 kg, *Paecilomyces hepiali* mycelium 40 kg.

EXAMPLE 9

The compound fungus polyose with effects of enhancing immunity was prepared with the following raw materials proportioned by weight: *Lentinus edodes* 35 kg, *Poria cocos* 50 kg, *Dictyophora indusiata* 120 kg, *Tremella fuciformis* 40 kg, *Paecilomyces hepiali* mycelium 35 kg.

EXAMPLE 10

The compound fungus polyose with effects of enhancing immunity was prepared with the following raw materials proportioned by weight: *Lentinus edodes* 50 kg, *Poria cocos* 80 kg, *Dictyophora indusiata* 150 kg, *Tremella fuciformis* 55 kg, *Paecilomyces hepiali* mycelium 50 kg.

In the above described examples, *Lentinus edodes, Dictyophora indusiata*, and *Tremella fuciformis* are off-the-shelf raw dietary material from the market and are listed in 《Dietary Ingredient Table of China》 (2004, edition). *Lentinus edodes* and *Dictyophora indusiata* are in compliance with GB 7096 《Hygienic Guide of Edible Fungus》. *Tremella fuciformis* is in compliance with GB 11675 《Hygienic Guide of Tremella Fuciformis》. *Poria cocos* is in compliance with the quality standard of 《Pharmacopoeias of People's Republic of China》 (2005, edition). *Paecilomyces hepiali* mycelium is consistent with the quality criteria WS3-C1-0001-95 (Z) 《Guide of Ministry of Public Health of People's Republic of China on fermented Chinese caterpillar fungus powder (CS-4)》.

The health dietary supplement prepared from compound fungus polyose according to the above examples as the main effective component by conventional technology, can take various dosage forms, such as capsules, tablets, powders, drug granules, oral liquid, and so on.

Study of Pharmacodynamics

Applicant tested the effectiveness of the compound fungus polyose powder which was prepared by conventional technology, according to the proportion of raw material listed in example 1. The test results are as follows:

1. Test Facility

Laboratory of Molecular Biology of College of Life Science of Sun Yat-sen.

2. Purpose of the Experiment

Study the immunologic enhancement of compound fungus.

3. Test Material 3.1 Specimen

The compound fungus polyose sample was prepared by Applicant. The sample had a brown powdered appearance and a unique aroma. Its polyose content is 30% (determined by sulfuric acid-phenol method).

3.2 Positive Control

Cyclophosphamide Injection, H.L.M.N H14023686, 0.2 g/bottle, produced by Shanxi Pude Medicine Co.

Polysaccharide-Peptide Capsule, H.L.M.N Z10980124, produced by Shanghai Xinkang Drug Manufactory.

3.3 Experimental Animals

NIH mice, SPF, 18-22 g, purchased from Guangdong Province Medical Laboratory Animals Center.

KM mice, SPF, 18-22 g, purchased from Guangdong Province Medical Laboratory Animals Center.

Guinea pigs: common, 300 g, purchased from Guangdong Province Medical Laboratory Animals Center.

3.4 Reagents and Drugs

S180 cell strain, purchased from cell bank of Guangdong province Medical Laboratory Animals Centre;

Methyl thiazolyl tetrazolium (MTT, sigma Co.), purchased from Guangzhou Weijia Biology Co. Ltd.

Trypsin (product of Shanghai Huamei Biology Company), purchased from Guangzhou Body Biology Co.

Dimethyl sulfoxide (DMSO), grade AR, Tianjin Body Chemical Engineering Co.

RPMI1640 Medium, supplied by Invitrogen Co.

Penicillin, North China Pharmaceutical Company, Ltd, H.L.M.N H13020657.

Streptomycin sulfate, North China Pharmaceutical Company, LTD, H.L.M.N H13020650.

Fetal bovine serum, supplied by Hyclone Laboratoreis Inc., Cat. NO: SH30401.01.

2,4-Dinitrochlorobenzene (DNCB), grade CP, produced by Shanghai NO1 Reagents Factory.

Acetone, grade AR, Guangdong Guanghua Chemistry Co.

$Na_2CO_3$, grade AR, produced by Guangzhou Reagent Factory.

Potassium cyanide, grade CP, produced by Guangzhou Reagent Factory.

Ferricyanatum kalium, grade AR, produced by Guangzhou Chemical Reagent Factory.

Mice CD3, 100 μg/1.0 ml, Cat: LHM3401, Lot#1385242B, and Mice NK1.1, 50 μg/0.5 ml, NO. LMM6604, Lot: 10903M, were produced by United States Invitrogen CALTAG LABORATORIES company.

10 ×FCM Lysing Solution (erythrocytolysin): 20 ml, product number: MAB-LS01, Lot: 0706610010, was produced by United States MULTISCIENCES BIOTEC ASSAYS Inc.

Paraformaldehyde: grade AR, produced by Tianjinn Yuanli Chemical Engineering co.

3.5 Test Equipment

BS110S electronic balance: produced by Beijing Saiduolisi Balance Co.; UV2102-PC scanning ultraviolet-visible spectrophotometer: produced by UNICO (Shanghai) Apparatus Co.; TG high speed centrifuge: produced by Shanghai Anting Apparatus Factory; CO2 Incubators, 2123TC: produced by United States SHELDON MANUFACTURING, INC; 37XB-Zinvert microscope: produced by Shanghai Optical Instrument NO. 6 Factory; 353 ELIASA: produced by Thermo Lab Systems; Plate type centrifuge; and flow cytometer.

3.6 Dosage Design

TABLE 1

| Dosage Design | | |
|---|---|---|
| Group | | Mice dosage (mg/kg) |
| Compound fungus polyose | low dosage | 50 mg/kg · d |
| | medium dosage | 100 mg/kg · d |
| | high dosage | 150 mg/kg · d |
| Cyclophosphamide injecta | | 100 mg/kg twice per week |
| Polysaccharide-peptide capsule | | 765 mg/kg |

Note: dosage of cyclophosphamide injecta is 100 mg/kg, twice a week, in 3-day intervals; is equivalent to 7 times the clinical dosage for a 60 kg adult, which is 850 mg/day; dosage of polysaccharide-peptide capsule is 765 mg/kg, is equivalent to 15 times the clinical dosage for 60 kg adult, which is 3.06 g/day.

4. Test Method 4.1 Effect on S180 Bearing Cancer Mice 85 healthy NIH mice, unisexual, were selected. Tumor cell S180 cell strain was recovered and 30 mice were selected as transplanted tumor species mice were observed for about 7-10 days. It is indicated that the tumor strain survived if ascites appeared in the peritoneal cavity of all the mice. The other 55 mice were used for solid tumor test.

At the beginning of the experiment, 20 mice with ascites were selected and sacrificed by pulling the cervical vertebrae on a sterilized bench, then the abdomens were sterilized with iodine tinctur, 75% alcohol q-tips in turn. The ascites were collected with 3 ml asepsis disposable syringe and put in asepsis dry conical flask and stored on the ice. The ascites of each mouse should be no less than 5 ml and about 7 ml of ascites were collected generally. It should be noted that the ascites collected were a milk-yellow or milk-white fluid, and the ascites with a larger quantity of RBC should be discarded. After the ascites were diluted 100 times, the cell density was measured to about $2 \times 10^7$/ml by the method of Trypan Blue count. The ascites were diluted with saline. The diluted ascites were subcutaneously injected, at a dosage of 0.2 ml, into the right armpit of each mouse.

After all qualified 55 mice were injected, they were randomly divided into 5 groups: the blank control group, the compound fungus polyose low-, medium-, and high-dosage groups, and the positive cyclophosphamide control group, respectively. 11 mice were in each group. Administration began from the second day; the mice in the blank control group were administered with equal-volume purified water with intragastric administration, the mice of three sample groups were administered with intragastric administration at the dosage as shown in Table 1, and the cyclophosphamide control group mice were intraperitoneally injected cyclophosphamide 100 mg/kg, 2 times per week. After 11 days of administration, all mice were sacrificed and their body weights, tumor weights, thymic weights, and spleen weights were measured. After the end of the experiment, statistical treatment of data was carried out to compare the difference among the groups.

Thymus (spleen) index=Thymus (spleen) weight/ Body weight×10 g

Body Weight Changes=Body weight after administration−Body weight before administration Inhibition ratio %=(Tumor weight in blank group− Tumor weight in treatment group)/Tumor weight in blank group×100%

4.2 Mice Immune Function Test
4.2.1 Mice Carbon Clearance Test 74 healthy KM male mice with body weights between 8 and 22 g were selected and randomly divided into 6 groups as the normal control group, cyclophosphamide model control group, compound fungus polyose low-, medium-, and high-dosage groups, and positive control group, respectively, with 11-13 mice in each group. Before beginning the experiment, mice of each group were administered with intragastric administration, one time a day, successively administered for 4 weeks. The normal control group and model control group mice were administered equal-volume purified water with intragastric administration. Dosages administered to the subject sample and polysaccharide-peptide capsule control groups are shown in Table 1. At the same time, the mice immunosuppression model was prepared with cyclophosphamide 60 mg/kg for injection. Except for the control group, mice of each group were intraperitoneally injected with cyclophosphamide at a dosage of 60 mg/kg, 2 times per week, in 3 day intervals.

30 minutes after the final administration, Chinese ink, which had been diluted 10 times with physiological saline and filtered, was injected in the caudal vein at a dosage of 0.2 ml/20 g. After both 2 minutes and 10 minutes of injection, using a suction tube pre-sodden by 1% Heparin Sodium, 20 µl of blood from the vena orbitalis posterior plexus was collected in 2 ml 0.1% $Na_2CO_3$ solution and agitated, shaded selection at wave length of A640 nm, then the optical density (OD) value was measured. At the end of the experiment, the mice were sacrificed and their livers, spleens, and thymic weights were measured. Value of clearance index K or correction factor α was determined by the following formula:

$K=(lgOD_1-lgOD_2)/(t_2-t_1)$

Notes: $OD_1$ and $OD_2$ is the OD of the blood samples collected at different times; $t_2-t_1$ is the time interval between the two blood samplings.

$\alpha=k^{1/3}\times$body weight/(liver weight+spleen weight)

Note If the variation of the spleen and liver weight was insignificant, only the k-value may be used.
4.2.2 Mice Tardive Hypersensitivity Test 86 healthy NIH male mice with body weights between 8-22 g were selected and randomly divided into 7 groups as: the control group, un-allergized control group, the cyclophosphamide model control group, the compound fungus polyose low-, medium-, and high-dosage groups, and the polysaccharide-peptide capsule control group, respectively, with 12-13 mice per group. Before beginning the experiment, mice of each group were administered with intragastric administration, one time a day, successively administered over 4 weeks. Mice of the normal control group, the un-allergized control group and the cyclophosphamide model control group were administered equal-volumes of purified water with intragastric administration. Dosages administered to the subject sample and polysaccharide-peptide capsule control groups were shown as Table 1. Except for the normal control group and the un-allergized control group, mice of other groups were injected intraperitoneally with cyclophosphamide 60 mg/kg, twice per week, in 3 day intervals, to prepare for the hypo-immunity mice model.

From the beginning of the 4th week's administration, the mice of all groups, apart from those in the un-allergized control group, had 50 µl of freshly prepared 7% DNCB Acetone Sesame oil (Acetone: Sesame oil=1:1) applied to their previously unhaired abdomen skins. Allergization was strengthened one more time the next day. After 5 days of allergization, 1% DNCB Acetone Sesame oil solution was evenly applied on the mice's right ears. The mice were sacrificed after 24 hours, about 8 mm of their right ears were punched with a puncher and weighed. The difference in weight between the left ear and right ears was defined as the swelling grade, which was the degree of DHT. Statistical treatment of the data was carried out to assess the difference between the groups.

4.2.3 Effect on Serum Erythrocytolysin of Hypoimmunity Mice 74 healthy KM mice with body weights between 18-22 g were selected and randomly divided into 6 groups: the normal control group, the cyclophosphamide model control group, compound fungus polyose low-, medium-, and high-dosage groups, and the positive control group, respectively, with 11-14 mice in each group. The mice were administered with pre-intragastric administrations before the experiment, one time a day, successively administered for 4 weeks. Mice of the normal control group and cyclophosphamide model control group were administered with equal-volume purified water with intragastric administration. Mice of the subject sample and positive control group were administered at the dosage shown by Table 1. From the beginning of the first week's administration, apart from the normal control group, mice of all groups were intraperitoneally injected with cyclophosphamide 60 mg/kg, 2 times per week, to create the hypoimmunity mice model.

After 30 minutes of the final administration, mice of each group were intraperitoneally injected with 0.2 ml SRBC suspensions 3:5 (V/V) to immune the animals. 5 days later, blood samples were collected from the eyes of the mice with orbital bleeding and the isolated serum was diluted with physiological saline 100 times. The erythrocytolysin was then determined.

One ml of the above-mentioned diluted serum was collected and added with 0.5 mil 10% SRBC suspensions and 1 ml 1:10 diluted guinea pig serum in succession. In a control tube, one ml of physiological saline was used and added with 0.5 ml 10% SRBC suspension and 1 ml 1:10 diluted guinea pig serum. The mixture was then maintained in a thermostatic water bath at 37° C. and quickly placed into ice water to terminate the reaction after incubation. The mixture was centrifuged for 10 minutes at 2000 rpm. One ml of clear supernatant liquid was collected and added to 3 ml of Due's reagent and agitated, held it for 10 minutes, then the OD value at the wavelength of 540 nm was measured using the control tube as reagent blank (to subtract the baseline). Another 0.25 ml of 10% SRBC suspension was diluted with Due's reagent to 4 ml, then agitated and held for 10 minutes. The OD value of SRBC $HD_{50}$ was then determined to at 540 nm. The $HD_{50}$ value of the sample was calculated according to the following formula:

Sample $HD_{50}$=(sample $OD/SRBC\ HD_{50}\ OD$)×dilution times (100)

4.2.4 Effect on Normal Mice T-Lymphocytes Proliferation and Transformation 66 healthy NIH male mice with body weights between 18-22 g were selected and randomly divided into 5 groups as: the normal control group, compound fungus polyose low-, medium-, and high-dosage groups, and the positive drug polysaccharide-peptide capsule control group, respectively, with 12-16 mice in each group. The mice were administered with an intragastric administration once a day, successively administered for 4 weeks.

Three batches of the following experiment were carried out. The mice's cervical vertebrae were pulled and each sacrificed after 30 minutes of the final administration. The same part of the spleen of each mouse was collected aseptically and placed in aseptic 1.5 ml EP tubes, added in 1 ml PBS solution. Tissues were softly cut to pieces using eye scissors. They were then blown and striked by suction-pipe to prepare for monoplast suspensions. The suspensions were filtered 2 times through 200 screen mesh and washed by PBS, centrifugated at 1000 rpm for 5 minutes each time. The supernatant was discarded and the cells suspended in 2 ml RPMI1640 culture solution. The viable count was made with trypan blue dye (survival ratio was above 95%) and cells concentration was adjusted at 1×107/ml. The cell suspension was then divided into 2 wells and transferred to a 24-well cultivation plate, 1 ml per well. 1 well was added with 75 μl ConA solution (equivalent 7.5 μg/ml) immediately. Another well was the control, which was placed in a 5% $CO_2$ incubator and cultivated for 72 hours at 37° C. 4 hours before the end of cultivation, suspending liquid in the 24-well cultivation plate was transferred to a 96-well cultivation plate as 3 well parallel samples with 100 μl per well. 50 μl RPMI1640 culture solution was then added. Then, MTT solution (5 mg/ml) at 50 μl/well was added, successively cultivated for 4 hours. After cultivation, the cells were centrifugated for 10 minutes at 1000 rpm with a plate-type centrifuge, supernatant was carefully removed, added in 100 μl DMSO solution per well, agitated lightly to dissolve crystallization and misce bene. OD value was determined by ELIASA at 450 nm and statistical treatment of the data was carried out to assess the difference between the groups.

4.2.5 Effect on Normal Mice NK Cell 51 healthy KM male mice with body weights between 18-22 g, were selected and randomly divided into 5 groups: the normal control group, compound fungus polyose low-, medium-, and high-dosage groups, and the positive drug polysaccharide-peptide capsule control group, respectively, with 10-11 mice per group. The mice were administered with intragastric administration 1 time per day, successively administered for 4 weeks. 30 minutes after the last administration, 0.5 ml blood samples in an EDTA-K2 anticoagulation tube were collected from the eyes of the mice by orbital bleeding in 2 groups and agitated. 50 μl peripheral blood was collected in a flow cytometer tube. NK1.1 antibody simple staining tube and CD3 antibody simple staining tube were designated respectively. 2.5 μl mice NK1.1 antibody and 2 μl CD3 antibody was added to the peripheral blood of the mice of each group. The mixture was protected from light and reacted for 15 minutes. 1 Ml of erythrocytolysin was then added. The mixture was protected from light and reacted for 10 minutes. The mixture was then centrifugated for 5 minutes at 1000 rpm and the supernatant was removed. The mixture was then washed once by 2 ml PBS, agitated, and centrifugated for 5 minutes at 1000 rpm. The supernatant was then discarded. The mixture was fixed with 0.5 ml of paraformaldehyde and maintained at 4° C. overnight. The mixture was resuspensed for measurement on the second day. Samples for which quadrant value with positive NK1.1 and negative CD3 were selected and statistical treatment was carried out to assess the difference between groups.

5. Test Results 5.1 Effect on S180 Cancer Bearing Mice

TABLE 2

Effect on S180 Cancer Bearing Mice

| Group | Dosage (mg/kg) | Tumor weight (g) | Thymus index (g/10 g) | Spleen index (g/10 g) | Anti-tumor ratio (%) |
|---|---|---|---|---|---|
| Blank control group | purified water | 1.4566 ± 0.1678 | 0.0249 ± 0.0054 | 0.0719 ± 0.0207 | — |
| Compound fungus polyose | low | 1.2583 ± 0.2124 | 0.0217 ± 0.0057 | 0.0664 ± 0.0137 | 15.3 |
|  | medium | 1.1288 ± 0.4542 | 0.0224 ± 0.0075 | 0.0676 ± 0.0111 | 22.0 |
|  | high | 0.9841 ± 0.5452* | 0.0227 ± 0.0054 | 0.0564 ± 0.0087 | 30.9 |
| Cyclophosphamide group | 100 | 0.0502 ± 0.0253*** | 0.0117 ± 0.0041 | 0.0322 ± 0.0190*** | 95.9 |

Note:
*P < 0.05,
**P < 0.01,
***P < 0.001,
$^\Delta$P > 0.05 (not shown) when compared with the blank control group As it is shown in table 2, the weights of the tumors in mice of the polyose compound fungus polyose treatment group were significantly decreased, wherein the weight difference between the high dosage group and the blank control group was statistically significant (P<0.05). For the positive control group, cyclophosphamide was shown to inhibit the growth of tumors, with an anti-tumor ratio of 95.9%, but the physiological conditions of the mice were poor: thymus and spleen showed obvious atrophy while both the tumor weight and spleen index showed a significant difference (P<0.001) when compared with the blank control group.

The above-described data indicated that the compound fungus polyose has the effect of inhibiting tumor growth and can improve the survival conditions of the mice by decreasing the degree of injury to their immune organs. The compound fungus polyose can play an attenuation and synergistic role through combination with chemotherapeutics.

5.2 Effect on Mice Immune Functions
5.2.1 Carbon Particle Clearance Test Results in Mice

TABLE 3

Effect on Carbon Particle Clearance in Mice

| Group | Dosage (mg/kg) | Animal number (n) | Body weight (g) | Liver weight (g) | Spleen weight (g) |
|---|---|---|---|---|---|
| Normal control group | purified water | 12 | 34.8 ± 1.8*** | 2.023 ± 0.194 | 0.100 ± 0.018*** |
| Cyclophosphamide model group | purified water | 13 | 31.4 ± 2.0 | 1.943 ± 0.303 | 0.065 ± 0.011 |
| Compound fungus polyose | low | 11 | 28.0 ± 1.9*** | 1.638 ± 0.245* | 0.057 ± 0.012 |
|  | medium | 13 | 29.1 ± 2.3* | 1.629 ± 0.186** | 0.062 ± 0.015 |
|  | high | 12 | 28.7 ± 2.6** | 1.695 ± 0.324 | 0.070 ± 0.021 |
| Polysaccharide-peptide capsule group | 765 | 13 | 27.9 ± 2.1*** | 1.539 ± 0.265*** | 0.060 ± 0.021 |

| Group | Dosage (mg/kg) | Thymic weight (g) | Clearance index K value | Correction factor α value |
|---|---|---|---|---|
| Normal control group | purified water | 0.090 ± 0.021*** | 0.075 ± 0.021*** | 6.89 ± 0.55*** |
| Cyclophosphamide model group | purified water | 0.019 ± 0.005 | 0.042 ± 0.019 | 5.34 ± 0.82 |
| Compound fungus polyose | low | 0.022 ± 0.010 | 0.055 ± 0.010* | 6.33 ± 0.67** |
|  | medium | 0.024 ± 0.008 | 0.067 ± 0.030* | 6.80 ± 0.95*** |
|  | high | 0.025 ± 0.007* | 0.077 ± 0.018*** | 7.13 ± 1.64** |
| Polysaccharide-peptide capsule group | 765 | 0.027 ± 0.006** | 0.080 ± 0.017*** | 7.64 ± 1.09*** |

It can be seen from Table 3 that the body and spleen weights of the mice of the cyclophosphamide model control group are less than those of the model control group. The thymus showed obviously atrophy, and clearance index K value and correction factor α value were significantly decreased, which were significantly different ($P<0.001$) when compared with the model control group. It is indicated that cyclophosphamide with intraperitoneal injection resulted in immune system injuries of the mice, and that the hypoimmunity model was prepared successfully. Liver weight of mice in the cyclophosphamide model control group showed no significant difference ($P>0.05$) compared with the control group. The result suggests that, at the dosage of 60 mg/kg, cyclophosphamide causes a lesser degree of injury to the liver of mice with a reduced immunity function, which is consistent with the situation when cyclophosphamide is clinically used in terms of safety and side-effects.

After the samples are administered for 4 weeks, the body weight of the mice in all groups increased slowly, so was the internal organ weight. The same situation occurred with the body weight and liver weight of the mice in the group treated with the polysaccharide-peptide capsule comparison. There was a significant difference ($P<0.05$, $P<0.01$, $P<0.001$) when compared with model control group. Perhaps, it is because hypoimmunity mice are not active, and the reduced activities plus daily administrations of the testing substance may affect their baseline food intake, thereby causing their body and spleen weights to increase slowly.

Compound fungus polyose increased the hypoimmunity mice's thymic weigh. The clearance index K and correction factor α were also evidently increased. The same effects were observed with the mice in the polysaccharide-peptide capsule group, whose thymic weight and K and α values were also increased. Those measured data showed a significant difference ($P<0.05$, $P<0.01$, $P<0.001$) when compared with those of the untreated control group. Such result indicates that the compound fungus polyose samples may increase both the amount and activity of the monocyte and macrophages in mice blood, thereby enhancing the non-specificity immune function of hypoimmunity mice.

5.2.2 Effect on Mice Delayed Hypersensitivity

TABLE 4

Effect on Delayed Hypersensitivity in Mice

| Group | | Dosage (mg/kg) | Animal number (n) | Swelling grade (%) | Enhancement ratio (%) |
|---|---|---|---|---|---|
| Normal control group | | equal volume | 12 | 4.43 ± 1.90*** | — |
| Non-allergized control group | | equal volume | 12 | 0.84 ± 0.44 | — |
| Cyclophosphamide model group | | equal volume | 13 | 0.99 ± 0.78 | — |
| Compound fungus | low dosage group | low | 13 | 1.03 ± 0.61 | 4.4 |
|  | medium dosage group | medium | 12 | 1.88 ± 1.08* | 89.9 |

TABLE 4-continued

Effect on Delayed Hypersensitivity in Mice

| Group | Dosage (mg/kg) | Animal number (n) | Swelling grade (%) | Enhancement ratio (%) |
|---|---|---|---|---|
| polyose   high dosage group | high | 12 | 2.59 ± 1.12*** | 161.6 |
| Polysaccharide-peptide capsule comparison group | 765 | 12 | 2.31 ± 1.32** | 133.3 |

Note:
*$P < 0.05$,
**$P < 0.01$,
***$P < 0.001$ when compared with the normal control group It is shown from the experiment results in Table 4 that the right ears of the un-allergized mice group showed no obvious swelling after being attacked, but the right ears of the normal control group mice show obvious swelling after being attacked. This indicates that when DNCB (dinitrochlorobenzene) makes contact with animal skin, it stimulates T-lymphocytes transferring and proliferating to allergized lymphocytes, which produce partly DTH reaction when attacked by an antigen. Concerning this process, there is a significant difference ($P<0.001$) between the two groups. The degree of ear swelling for the cyclophosphamide model control group mice is the least, due to its strong inhibitory effect on T-lymphocytes, causing a reduced number of T-lymphocytes and thus reduced immune function of the mice. After 4 weeks of administration, ear swelling appeared to increase variably for different groups; wherein there are significant differences in the degree of ear swelling between the untreated control group and the treatment groups (with medium and high dosage of the compound fungus polyose as well as the positive control group, $P<0.05$, $P<0.01$, $P<0.001$, respectively), the effect on swelling of the low, medium, and high dosage of the compound fungus polyose is 4.4%, 89.9% and 161.6%, respectively.

5.2.3 Effect on serum erythrocytolysin in mice

From the experiment results in Table 5, it is shown that the $HC_{50}$ value of the mice in the cyclophosphamide treated model control group was significantly decreased when compared with the mice in the normal control group ($P<0.001$), indicating that injecting cyclophosphamide can result in the occurrence of humoral immunosuppression in mice and significant reduction in the production of serum erythrocytolysin. After 4 weeks of administration of the treatment, the HC50 of mice in each group showed varying degrees of increase, wherein HC50 of the mice in the high-dosage compound fungus polyose group and the positive control group mice, had a significant difference ($P<0.05$, $P<0.01$, $P<0.001$) when compared with the model control group, the increasing ratio for the groups given with low, medium and high dosage of the compound fungus polyose was 24.5%, 50.0%, and 72.4%, respectively; the increasing ratio for the positive control group is 133.5%. It is indicated that the compound fungus polyose can overcome the antibody level that cases reduced immune function of the mice injected with cyclophosphamide.

TABLE 5

Effect on Serum Erythrocytolysin in Mice

| Group | | Dosage (mg/kg) | Animal number (n) | HC50 | Enhancement ratio (%) |
|---|---|---|---|---|---|
| Normal control group | | equal-volume | 11 | 61.22 ± 11.89*** | — |
| Cyclophosphamide model group | | equal-volume | 14 | 17.73 ± 8.92 | — |
| Compound | low dosage | low | 13 | 22.08 ± 12.00 | 24.5 |
| fungus | medium dosage | medium | 12 | 26.59 ± 14.58 | 50.0 |
| polyose | high dosage | high | 13 | 30.56 ± 12.80** | 72.4 |
| Polysaccharide-peptide capsule control group | | 765 | 11 | 41.40 ± 16.14*** | 133.5 |

Note:
*$P < 0.05$,
**$P < 0.01$,
***$P < 0.001$ when compared with the normal control group 5.2.4 Effect on T-Lymphocytes proliferation and transformation in normal mice

TABLE 6

Effect on Proliferation and Transformation of T-Lymphocytes

| Group | | Dosage (mg/kg) | Animal number (n) | OD difference | Enhancement ratio (%) |
|---|---|---|---|---|---|
| Normal control group | | equal-volume | 16 | 0.204 ± 0.099 | — |
| Compound | low dosage | 50 | 13 | 0.388 ± 0.169*** | 90.2 |
| fungus | medium dosage | 100 | 13 | 0.414 ± 0.217*** | 102.9 |
| polyose | high dosage | 150 | 12 | 0.429 ± 0.250*** | 110.3 |
| Polysaccharide-peptide capsule comparison group | | 765 | 12 | 0.373 ± 0.234*** | 82.8 |

Note:
*P < 0.05,
**P < 0.01,
***P < 0.001 when compared with the normal control group When cultured with Concanavalin (ConA) or other mitogens or specificity antigens, T-Lymphocytes can be transformed to lymphoblast and lead to vigorous proliferation. Viable cells, especially proliferating cells, disintegrate MTT into carmine crystallization and show colors through mitochondria hydrolase. The optical density value can reflect the condition of cell proliferation.

It is shown from the experiment results in Table 6 that the optical density (OD) is lowest for the normal control group. In comparison, the OD values was significantly increased for the groups given low, medium and high dosage of the compound fungus polyose (P<0.05, P<0.01, P<0.001, respectively), and the increasing ratio was 90.2%, 102.9%, 110.3%, respectively. This indicates that that the compound fungus polyose and positive drug polysaccharide-peptide capsule can enhance proliferation and transformation of T-lymphocytes induced by ConA in mice spleen, thus having a better cytoimmunity regulation function.

5.2.5 Effect on NK cells in normal mice

TABLE 7

Effects on NK cell activities in normal mice

| Group | | Dosage (mg/kg) | Animal number (n) | NK (%) | Enhancement ratio (%) |
|---|---|---|---|---|---|
| Normal control group | | equal-volume | 11 | 1.92 ± 1.82 | — |
| Compound | low dosage group | 50 | 10 | 2.24 ± 1.68 | 16.7 |
| fungus | medium dosage group | 100 | 10 | 3.52 ± 1.84 | 83.3 |
| polyose | high dosage group | 150 | 10 | 4.06 ± 2.52* | 111.4 |
| Polysaccharide-peptide capsule comparison group | | 765 | 10 | 3.23 ± 2.13 | 68.2 |

Note:
*P < 0.05,
**P < 0.01,
***P < 0.001,
$^\Delta$P > 0.05 (not shown) when compared with the normal control group NK cell possess the spontaneous cell mediated cytotoxicity, which has natural killing abilities existing in the organism, although its cytotoxic activity is not as potent as T cells and K cells, it acts quickly and is one of the important non-specificity defense mechanisms. NK cells can destroy and dissolve cells without any antigenic stimulus and complement participation. At present the flow cytometry is the method used clinically to determine the amount of NK cells labeled with specificity antibody in peripheral blood.

For result presented in the Table 7, NK % refers to the population of the NK cells which are NK1.1 positive while CD3 negative. The NK % value of the mice in the groups given with low, medium, or high dosage of the compound fungus is evidently increased. The NK % value showed statistically significant difference when compared with untreated normal control group (P<0.05), indicating that compound fungus polyose may have a good immuno-regulation effect by stimulating NK cell proliferation.

6. Conclusion

In sum, as presented in the above, the experimental data on the compound fungus polyose of the present invention, i.e., the transplantation tumor test, carbon clearance test, DTH test, serum erythrocytolysin test, T-Lymphocytes proliferation and transformation test and NK cell test, all indicate that the compound fungus polyose possesses immunologic enhancement activities and can be classified as such according to 《health food analysis and assessment technique standard》 (the 2003 edition) by the Ministry of Health of the People's Republic of China.

What is claimed is:

1. A composition for enhancing immunity comprising, by weight ratio, *Lentinus edodes* 8-100, *Poria cocos* 15-100, *Dictyophora indusiata* 0-200, *Tremella fuciformis* 15-80, and *Paecilomyces hepialid* mycelium 2-50, each in the form of a powdered raw material.

2. The composition according to claim 1, wherein the composition comprises by weight ratio *Lentinus edodes* 10~50,

*Poria cocos* 45~80, *Dictyophora indusiata* 30~150, *Tremella fuciformis* 25~55, and *Paecilomyces hepiali* mycelium 10~50.

3. The composition according to claim 1, wherein the composition comprises by weight ratio *Lentinus edodes* 30, *Poria cocos* 60, *Dictyophora indusiata* 90, *Tremella fuciformis* 40, and *Paecilomyces hepiali* mycelium 20.

4. The composition according to claim 1, wherein the composition comprises by weight ratio *Lentinus edodes* 10, *Poria cocos* 80, *Dictyophora indusiata* 100, *Tremella fuciformis* 60, and *Paecilomyces hepiali* mycelium 45.

5. The composition according to claim 1, wherein the composition comprises by weight ratio *Lentinus edodes* 40 *Poria cocos* 80, *Dictyophora indusiata* 70, *Tremella fuciformis* 50, and *Paecilomyces hepiali* mycelium 25.

6. The composition according to claim 1, wherein the composition comprises by weight ratio *Lentinus edodes* 60 *Poria cocos* 100, *Dictyophora indusiata* 120, *Tremella fuciformis* 20, and *Paecilomyces hepiali* mycelium 20.

7. The composition according to claim 1, wherein the composition comprises by weight ratio *Lentinus edodes* 80 *Poria cocos* 50, *Dictyophora indusiata* 130, *Tremella fuciformis* 30, and *Paecilomyces hepiali* mycelium 15.

8. The composition according to claim 1, wherein the composition comprises by weight ratio *Lentinus edodes* 90, *Poria cocos* 30, *Dictyophora indusiata* 70, *Tremella fuciformis* 30, and *Paecilomyces hepiali* mycelium 35.

9. The composition according to claim 1, wherein the composition comprises by weight ratio *Lentinus edodes* 15, *Poria cocos* 50, *Dictyophora indusiata* 30, *Tremella fuciformis* 30, and *Paecilomyces hepiali* mycelium 20.

10. The composition according to claim 1, wherein the composition comprises by weight ratio *Lentinus edodes* 70, *Poria cocos* 90, *Dictyophora indusiata* 180, *Tremella fuciformis* 70, and *Paecilomyces hepiali* mycelium 40.

11. The composition according to claim 1, wherein the composition comprises by weight ratio *Lentinus edodes* 35, *Poria cocos* 50, *Dictyophora indusiata* 120, *Tremella fuciformis* 40, and *Paecilomyces hepiali* mycelium 35.

12. The composition according to claim 1, wherein the composition comprises by weight ratio *Lentinus edodes* 50, *Poria cocos* 80, *Dictyophora indusiata* 150, *Tremella fuciformis* 55, and *Paecilomyces hepiali* mycelium 50.

* * * * *